(12) United States Patent
Saeed et al.

(10) Patent No.: US 11,251,031 B1
(45) Date of Patent: Feb. 15, 2022

(54) SYSTEMS AND METHODS FOR MEASURING SIMILARITY BETWEEN MASS SPECTRA AND PEPTIDES

(71) Applicants: Fahad Saeed, Miami, FL (US); Muhammad Usman Tariq, Miami, FL (US)

(72) Inventors: Fahad Saeed, Miami, FL (US); Muhammad Usman Tariq, Miami, FL (US)

(73) Assignee: THE FLORIDA INTERNATIONAL UNIVERSITY BOARD OF TRUSTEES, Miami, FL (US)

(*) Notice: Subject to any disclaimer, the term of this patent is extended or adjusted under 35 U.S.C. 154(b) by 0 days.

(21) Appl. No.: 17/339,070

(22) Filed: Jun. 4, 2021

(51) Int. Cl.
*H01J 49/36* (2006.01)
*H01J 49/00* (2006.01)
*G01N 33/68* (2006.01)

(52) U.S. Cl.
CPC ...... *H01J 49/0036* (2013.01); *G01N 33/6848* (2013.01)

(58) Field of Classification Search
CPC .................. H01J 49/0036; G01N 33/6848
USPC .............................. 250/281, 282; 702/27, 28
See application file for complete search history.

(56) References Cited

U.S. PATENT DOCUMENTS

2020/0302224 A1* 9/2020 Jaganathan ............. G06F 16/58

* cited by examiner

*Primary Examiner* — Michael Maskell
(74) *Attorney, Agent, or Firm* — Saliwanchik, Lloyd & Eisenschenk

(57) ABSTRACT

Systems and methods for measuring cross-modal similarity between mass spectra and peptides are provided. A deep learning network can be used and, by training on a variety of labeled spectra, the network can embed both spectra and peptides onto a Euclidean subspace where the similarity is measured by the L2 distance between different points. The network can be trained on a novel loss function, which can calculate the gradients from sextuplets of data points.

20 Claims, 9 Drawing Sheets

SYSTEMS AND METHODS FOR MEASURING SIMILARITY BETWEEN MASS SPECTRA AND PEPTIDES

GOVERNMENT SUPPORT

This invention was made with government support under 1R01GM134384 awarded by National Institute of Health (NIH). The government has certain rights in the invention.

BACKGROUND

Mass spectrometry (MS) proteomics data is typically identified using database search algorithms purely based on numerical techniques (see also FIG. 1). These numerical techniques operate by comparing the experimental spectra to the simulated spectra generated from theoretical peptides using a simple simulator. The experimental spectra are matched against the theoretical ones using one of many available heuristic scoring-functions including dot product, shared peak count, and ion matches. Other peptide identification techniques, such a de novo algorithms, also deduce peptides directly from experimental spectra with varying degrees of success.

No single related art heuristic from database search techniques can claim being the most accurate strategy. Computational techniques for identification of peptides using database search exist (see also FIG. 2), as do de novo algorithms. However, peptide identification problems are well-known and prevalent, including but not limited to misidentifications or no identifications for peptides, false discovery rate, and inconsistencies between different search engines. De novo algorithms have lower average accuracy (<35%) than database search algorithms (30-80%). Lack of quality assessment benchmarks makes the accuracy exhibited from these database search tools highly dependent on the data. Two major sources of heuristic errors that are introduced in the numerical database search algorithms are the way in which the peptide deduction takes place (i.e., simulation of the spectra (from peptides)) and the peptide spectrum match scoring-function. The simplistic and a priori nature of the scoring mechanism neglects the MS data (and the database) that are under consideration, leading to variable quality peptide deductions.

BRIEF SUMMARY

Embodiments of the subject invention provide novel and advantageous systems and methods for measuring cross-modal similarity between mass spectra and peptides (e.g., for peptide deduction). A deep learning architecture and/or network (e.g., a deep neural network) can be used for measuring the cross-modal similarity between spectra and peptides. By training on a variety of labeled spectra, the network can embed both spectra and peptides onto a Euclidean subspace where the similarity is measured by the L2 distance between different points, where the L2 distance d between two vectors p and q of length n is given by $$d = \sqrt{\sum_{i=1}^{n} (p_i - q_i)^2}.$$

The network can be trained on a novel loss function (which can be referred to as a SNAP-loss function), which can calculate the gradients from sextuplets of data points. Each sextuplet can include a positive pair (spectrum, label peptide) and four negative examples. Training the network this way can result in optimal performance.

In an embodiment, a system for measuring cross-modal similarity between mass spectra and peptides can comprise a processor and a (non-transitory) machine-readable medium in operable communication with the processor and having instructions stored thereon that, when executed by the processor, perform the following steps: receiving a set of mass spectra data and a set of peptide data into a network comprising a spectral sub-network (SSN) and a peptide sub-network (PSN); inputting the set of mass spectra data into the SSN, the SSN comprising two fully connected hidden layers and an L2 normalization output layer; inputting the set of peptide data into the PSN, the PSN comprising one bi-directional long short-term memory (Bi-LSTM) layer and two fully connected layers; processing the set of mass spectra data in the SSN and embedding it on a surface of a unit hypersphere in a Euclidean subspace; processing the set of peptide data in the PSN and embedding it on the surface of the unit hypersphere in the Euclidean subspace; and matching mass spectra from the set of mass spectra data with peptides from the set of peptide data, using an L2-distance-based similarity measure. The instructions when executed can further train the network on a loss function that calculates gradients from sextuplets of data points of the set of mass spectra data, the set of peptide data, or both. The training of the network can comprise calculating a loss value by generating the sextuplets after each forward pass, and each sextuplet can comprise a positive pair (Q, P), a negative pair $(Q_N, P_N)_Q$ for Q, and a negative pair $(Q_N, P_N)_P$ for P, where Q is an anchor spectrum and P is a positive peptide. Each negative pair can be selected via an online hardest negative mining process, in which negative spectra and peptides that are closest to Q and P are selected for a given batch after each forward pass. The PSN can further comprise an embedding layer before the Bi-LSTM layer, and the embedding layer can use a vocabulary size of 20 or 30 to construct embeddings. The Bi-LSTM layer can have a hidden dimension of 512, and the two fully connected layers of the PSN can be after the Bi-LSTM layer and/or can comprise a first layer with a size of 1024×512 and/or a second layer with a size of 512×256. The two fully connected hidden layers of the SSN can comprise a first layer with a size of 80,000×1024 and/or a second layer with a size of 1024×256. The two fully connected hidden layers of the SSN can utilize a rectified linear activation function (ReLU). The SSN can further comprise a dropout mechanism with a probability of 0.3 after a first layer of the two fully connected hidden layers of the SSN and before a second layer of the two fully connected hidden layers of the SSN. The two fully connected layers of the PSN can utilize a ReLU. The PSN can further comprise: a first dropout mechanism with a first probability of 0.3 after the Bi-LSTM layer and before a first layer of the two fully connected layers of the PSN; and/or a second dropout mechanism with a second probability of 0.3 after the first layer of the two fully connected layers of the PSN and before a second layer of the two fully connected layers of the PSN.

In another embodiment, a method for measuring cross-modal similarity between mass spectra and peptides can comprise: receiving (e.g., by a processor) a set of mass spectra data and a set of peptide data into a network comprising an SSN and a PSN; inputting (e.g., by the processor) the set of mass spectra data into the SSN, the SSN comprising two fully connected hidden layers and an L2 normalization output layer; inputting (e.g., by the processor)

the set of peptide data into the PSN, the PSN comprising one Bi-LSTM layer and two fully connected layers; processing (e.g., by the processor) the set of mass spectra data in the SSN and embedding it on a surface of a unit hypersphere in a Euclidean subspace; processing (e.g., by the processor) the set of peptide data in the PSN and embedding it on the surface of the unit hypersphere in the Euclidean subspace; and matching (e.g., by the processor) mass spectra from the set of mass spectra data with peptides from the set of peptide data, using an L2-distance-based similarity measure. The method can further comprise training (e.g., by the processor) the network on a loss function that calculates gradients from sextuplets of data points of the set of mass spectra data, the set of peptide data, or both. The training of the network can comprise calculating a loss value by generating the sextuplets after each forward pass, and each sextuplet can comprise a positive pair (Q, P), a negative pair $(Q_N, P_N)_Q$ for Q, and a negative pair $(Q_N, P_N)_P$ for P, where Q is an anchor spectrum and P is a positive peptide. Each negative pair can be selected via an online hardest negative mining process, in which negative spectra and peptides that are closest to Q and P are selected for a given batch after each forward pass. The PSN can further comprise an embedding layer before the Bi-LSTM layer, and the embedding layer can use a vocabulary size of 20 or 30 to construct embeddings. The Bi-LSTM layer can have a hidden dimension of 512, and the two fully connected layers of the PSN can be after the Bi-LSTM layer and/or can comprise a first layer with a size of 1024×512 and/or a second layer with a size of 512×256. The two fully connected hidden layers of the SSN can comprise a first layer with a size of 80,000×1024 and/or a second layer with a size of 1024×256. The two fully connected hidden layers of the SSN can utilize a ReLU. The SSN can further comprise a dropout mechanism with a probability of 0.3 after a first layer of the two fully connected hidden layers of the SSN and before a second layer of the two fully connected hidden layers of the SSN. The two fully connected layers of the PSN can utilize a ReLU. The PSN can further comprise: a first dropout mechanism with a first probability of 0.3 after the Bi-LSTM layer and before a first layer of the two fully connected layers of the PSN; and/or a second dropout mechanism with a second probability of 0.3 after the first layer of the two fully connected layers of the PSN and before a second layer of the two fully connected layers of the PSN.

DETAILED DESCRIPTION

Figure 1:
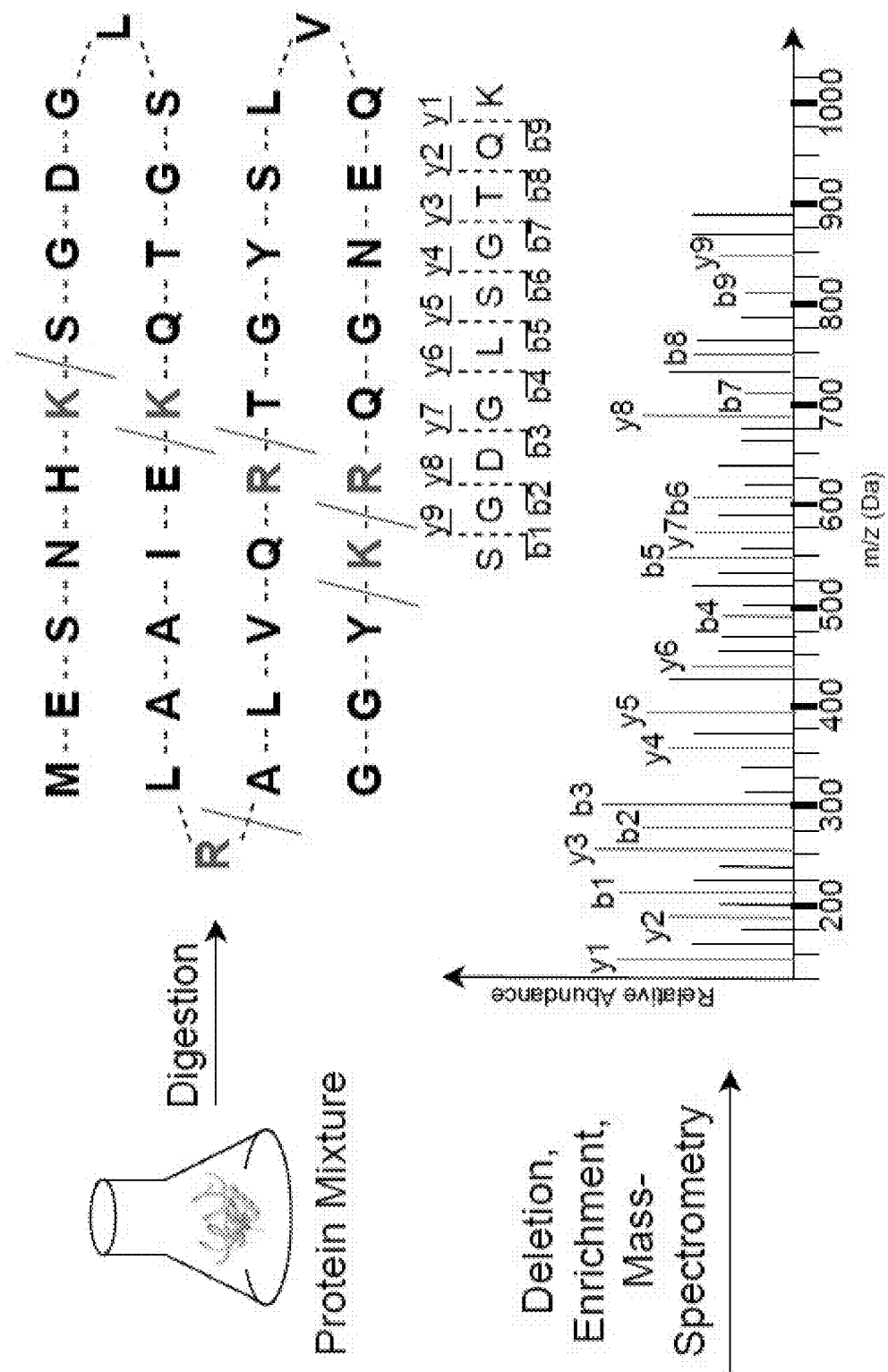
FIG. 1 shows a schematic view of a process of generating tandem mass spectrometry (MS/MS) spectra from a protein mixture using mass spectrometry (MS) analysis. Protein in the mixture are broken into peptides using an enzyme (e.g., trypsin), which breaks the protein strings at K and R bases generating peptides of varying sizes. This peptide mixture is then refined, and peptides are moved through a mass spectrometer, which generates an MS/MS spectrum for each different peptide.
Figure 2:
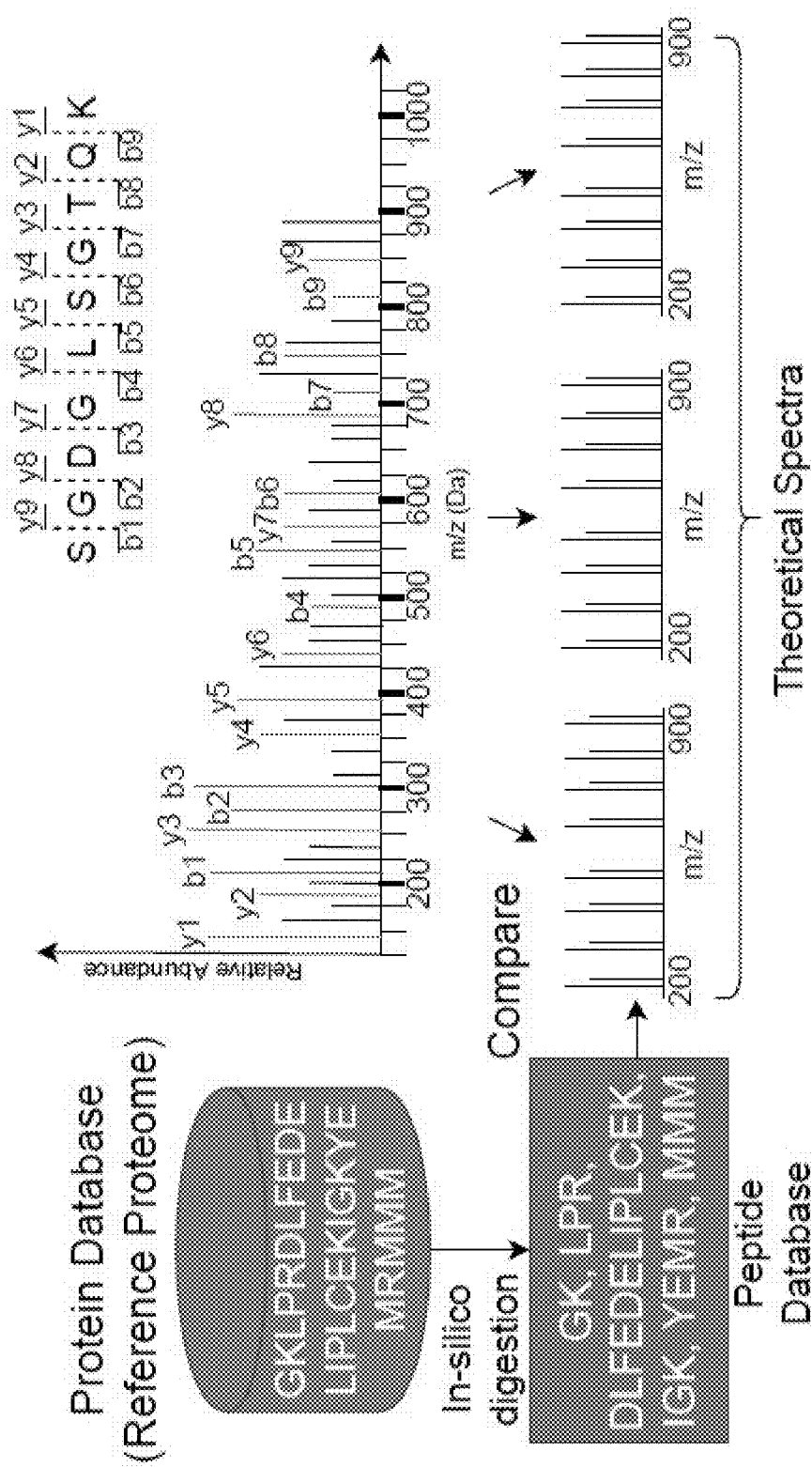
FIG. 2 shows a schematic view of proteomics flow. In silico digestion of the protein database is performed to generate peptides. These peptides are then converted to the theoretical spectra and compared against the experimental spectra.

Embodiments of the subject invention provide novel and advantageous systems and methods for measuring cross-modal similarity between mass spectra and peptides (e.g., for peptide deduction). A deep learning architecture and/or network (e.g., a deep neural network), which can be referred to herein as SpeCollate, can be used for measuring the cross-modal similarity between spectra and peptides. By training on a variety of labeled spectra, the network can embed both spectra and peptides onto a Euclidean subspace where the similarity is measured by the L2 distance between different points, where the L2 distance d between two vectors p and q of length n is given by $$d = \sqrt{\sum_{i=1}^{n} (p_i - q_i)^2}.$$

The network can be trained on a novel loss function (which can be referred to as a SNAP-loss function), which can calculate the gradients from sextuplets of data points. Each sextuplet can include a positive pair (spectrum, label peptide) and four negative examples. Training the network this way can result in optimal performance.

Related art peptide spectrum matching/scoring algorithms rely on intermediate approximations to compare mass spectra against peptides. These steps include simulating theoretical spectra from peptides and then comparing theoretical spectra against mass spectra using heuristic scoring functions. The simulation step tries to approximate the mass spectrometry (MS) process, which results in significant information loss, introducing sources of error. Similarly, the scoring functions are not appropriately designed to provide an optimum match; rather, only empirical evidence is given in reference to their utility. These scoring functions provide sub-optimal performance. Embodiments of the subject invention overcome these shortcomings by learning the similarity function between peptides and mass spectra directly from the data without the need to simulate spectra or design a scoring function. This goal is achieved by a novel loss function that ensures optimal training performance helps achieve this goal. Comparison across a variety of data points shows the superiority of SpeCollate compared to related art scoring functions (e.g., XCorr and Hyperscore).

SpeCollate can include two sub-networks, which can be referred to as a spectrum sub-network (SSN) and a peptide sub-network (PSN). The SSN can process spectra, and the PSN can process peptides.

The SSN can include two fully connected layers. The first layer can have a size of, for example, 80,000×1024, though embodiments are not limited thereto; and the second layer can have a size of, for example, 1024×256, though embodiments are not limited thereto. Both layers can be activated by the rectified linear activation function (ReLU), and the output of the last layer can be passed through an L2 normalization layer so that embeddings lie on the surface of the unit hypersphere. Dropout (e.g., with a probability of 0.3) can be used after the first layer. The input spectra to the SSN can be in the form of dense vectors of normalized intensities such that the intensity value at each m/z can be placed in an appropriate bin (e.g., a bin of width 0.1 Da). The bin index for a given m/z can be calculated by, for example, rounding m/z*10 to the nearest integer. In this format, the maximum m/z is limited to 8,000.

The PSN can include a bidirectional long short-term memory network (Bi-LSTM), followed by two fully connected layers; the first fully connected layer can have a size of, for example, 1024×512, though embodiments are not limited thereto; and the second fully connected layer can have a size of, for example, 512×256, though embodiments are not limited thereto. The Bi-LSTM layer can have a hidden dimension (e.g., of 512), and the output from the forward and the backward pass can be concatenated to get a vector (e.g., a 1024 dimension vector). The Bi-LSTM layer can be preceded by an embedding layer (e.g., with an embedding size of 256 or 512). This layer can embed each amino acid in the peptide sequence in an array (e.g., in a 256 dimension array). A vocabulary size can be utilized (e.g., a vocabulary size of 30 can be used to encode 20 amino acids, blank space, and 9 modifications). ReLU activation can be used for both fully connected layers, and dropout (e.g., with a probability of 0.3) can be used after the Bi-LSTM and the first fully connected layer. L2 normalization can be used at the output of the PSN so that the embedded vectors lie at the surface of a unit hypersphere.

In many embodiments, the network can be trained using a novel, custom-designed loss function (SNAP-loss function), which can calculate the loss value on sextuplets of data points. The sextuplets can be generated online after each forward pass of the batch and can include a positive pair (anchor mass spectrum and the peptide label) and four negative examples (e.g., can include exactly one positive pair and four negative examples). The four negative examples can include two spectra and two peptides, such that one spectrum and peptide is closest to the anchor spectrum and one spectrum and peptide is closest to the label peptide among all the negative examples in the batch. The loss can be calculated by taking the difference of the positive distance from all four negative distances and adding the results. Here, the positive distance can be defined as the squared L2 distance between the anchor spectrum and the peptide label while the negative distance can be defined as the distance between the anchor spectrum/label peptide and one of the negative examples. The total loss over all training examples in a batch can be used, and a margin value of 0.2 can be added to the difference calculation of each negative example within a sextuplet to avoid situations where the positive and the negative distances are similar. Selecting the hardest negative examples can ensure the selection of the hardest examples so that the training process is swift and optimal. An optimizer (e.g., Adam optimizer) can be used for the training, e.g., with a learning rate of 0.0001 and a weight decay of 0.00001.

Two major shortcomings in related art systems and methods are that: the simulation step tries to approximate the stochastic mass spectrometry process and as a result, incurs numerous inaccuracies; and the heuristic scoring functions are not designed by strong scientific backing, and instead only empirical evaluation is provided for their accuracies indicating potential sub-optimal performance. Embodiments of the subject invention overcome these shortcomings by eliminating these limiting factors and directly comparing mass spectra and peptides. A main challenge overcome by embodiments of the subject invention is comparing peptide strings against numerical arrays of mass spectra, which is addressed by the deep similarity network with two different branches (SSN and PSN), in which one branch processes mass spectra and the other processes the peptides. This is done in such a way that the resultant output of both branches is in the form of vectors that can be easily compared. Related art loss functions only provide a limited training performance due to the dual nature of the data in embodiments of the subject invention. This issue can be overcome by using the novel loss function (SNAP-loss) of embodiments of the subject invention, which optimizes the training by taking into account multiple data points from both data modalities.

Figure 3:
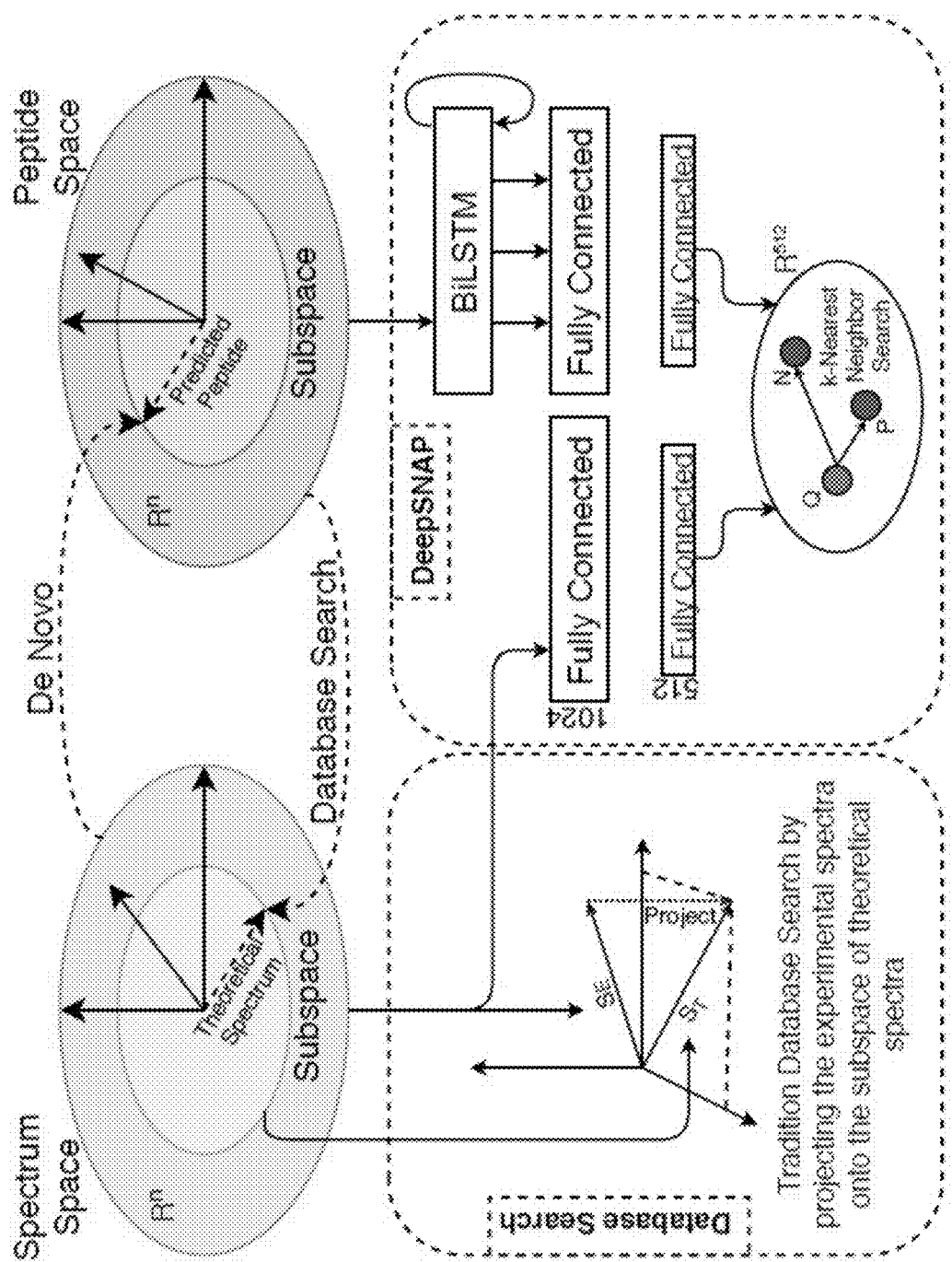
FIG. 3 shows a schematic view of space transition methods—de novo and database search that try to transform one space to another. This is prone to error and uncertainty as a lot of information can be missed. In contrast, embodiments of the subject invention can learn same-sized embeddings for both peptides and spectra by projecting them to a shared Euclidean space.

Peptides and their corresponding tandem mass spectrometry (MS/MS) spectra lie in vastly distinct spaces. Peptides include a string of (typically twenty) alphabets (each representing an amino acid) while spectra are a series of floating point numbers generated by complex and a rather stochastic fragmentation process. Transitioning in between spaces can only hope to approximate the counterpart projection as manifested by the existing techniques. De novo projects spectra onto a sub-peptide-space but with underwhelming accuracy as the spectra are mostly noisy and necessary information is missing. Similarly, in peptide-spectrum scoring methods, peptides are projected onto sub-spectral-space and the similarity is measured by projecting the experimental spectra onto the same subspace (dot-product) for comparison, as shown in FIG. 3. Although the database search process is relatively more accurate than related art de novo algorithms, the quality of the output is contingent on the quality of the experimental and projected theoretical spectra. Also, simulation of stochastic processes is prone to errors. Therefore, a need exists for eliminating the problems involved in space transitioning.

Related art database search tools typically provide a simulator to generate spectra, containing b and y peaks (sometimes a, c, x, and z) from the theoretical peptides. Some simulators also provide options to generate peaks with different neutral losses ($NH_3$, $H_2O$), immonium ions, and isotope ions. These simulators incur numerous deficiencies due the inherent complexities of the MS process causing misidentification of multiple features. These include unaccounted peaks, missing peaks, falsely-identified true and noisy peaks, peak intensities, neutral losses, isotopic peaks, and noise characteristics. As a result, the simulated spectra only manage to span a sub-space of experimental spectra (see also FIG. 3). One of the advantages of embodiments of the subject invention is eliminating the need of using a simulator as an intermediate step in the peptide-spectrum match process. Instead, the experimental spectra and their corresponding theoretical peptide string can be matched directly (without the use of a simulator as an intermediate step) by learning the similarity function between them from huge sets of labeled data (e.g., labeled data available in, for example, National Institute of Standards and Technology (NIST) and MassIVE (massive.ucsd.edu/).

Although simulators somewhat help improve the database search process in related art systems and methods, they only address half of the challenge (i.e., the simulation of spectra), while the heuristic based scoring function is still the limiting factor. The choice of scoring function is not backed up by any strong scientific reasoning and often does not yield the most optimal results. Different fragmentation patterns yield different types of ions that can assist or resist peptide spectrum matching. The comparison of complex fragmentation spectra is not straightforward and leads to unreliable outcomes. SpeCollate overcomes this problem by learning a multimodal similarity (or scoring) function by training on highly accurate data. By processing data from different modalities using different types of networks (i.e., spectra using SSN and peptides using PSN), it is able to extract the most useful features needed for proper matching. Also, the novel SNAP-loss objective function allows the network to learn the optimal features and generalize for much broader data sets.

Proteomics is a big-data field presenting newer challenges in terms of data handling and search space reduction. In meta-proteomics and proteogenomics, the search space can reach multiple terabytes in size. The problem becomes even worse for related art database search engines because the theoretical spectra database size grows multiple times larger than the peptide database due to generating different theoretical spectra for each charge and modification per peptide. In embodiments of the subject invention, as SpeCollate processes the original peptide strings and learns the similarity function from the labeled data, the training process can be designed in such a way that different charged spectra match to the original peptide string without the need to consider each charge separately. In this way, the peptide database size is reduced by orders of magnitudes in embodiments of the subject invention, improving the search speed and reducing false negatives due to search space inflation.

When learning a similarity (or scoring) function, it would be ideal to retain all the features that improve the similarity measure while abolishing the useless ones. SpeCollate approaches this solution by projecting both peptides and spectra onto a shared Euclidean space. This is accomplished by learning embeddings of equal size for both—spectra and peptides—in such a way that their similarity is directly proportional to L2 distance in the resultant Euclidean space. This addresses both above mentioned fundamental problems by finding a middle ground between two extremes (de novo and database search) and simplifying the comparison. Deep learning can be used, in embodiments of the subject invention, to learn the similarity function by reducing the spectra and peptides to a lower dimension embedded feature vectors. By using a combination of different networks, the exact features are extracted that are required to confidently assign spectra to their corresponding peptides.

Embodiments of the subject invention utilize a similarity network (SpeCollate) and/or novel loss function (SNAP-loss) to learn a similarity function for peptide-spectrum matches. A fixed sized embedding of variable length experimental spectra can be learned, as can peptide strings, in such a way that a given spectrum and its corresponding peptide are projected close to each other in the shared subspace. The network can include two sub-networks—an SSN including (or consisting of) two fully connected layers and a PSN including (or consisting of) one bi-directional LSTM followed by two fully connected layers.

The training process can take two sets of data points as inputs (i.e., the sparse spectrum vectors and encoded peptide strings can be taken as inputs). The loss value can be calculated generating sextuplets, after each forward pass, including (or consisting of) a positive pair (Q, P), a negative pair $(Q_N, P_N)_Q$ for Q, and a negative pair $(Q_N, P_N)_P$ for P, where Q is the anchor spectrum and P is the positive peptide. The negative pairs can be selected via online hardest negative mining to make the training process more efficient and faster. In this process, the negative spectra and peptides that are closest to Q and P are selected for a given batch after each forward pass. A number of other features can also be used to generalize the training of the network through multitask-learning, including the fragment ion sequences in the spectrum, the precursor mass, charge state, fragmentation process, and/or others. In addition to improving the similarity metrics, the learned embeddings work well for dimensionality reduction by projecting the original spectrum onto a smaller subspace as well as conserving the features that matter the most for similarity. Moreover, the L2-distance-based similarity measure is flexible enough to match multiple modified spectra to their original (unmodified) peptides. This is obtained by generating training data containing positive pairs including a modified spectrum and the corresponding unmodified peptide.

Figure 4:
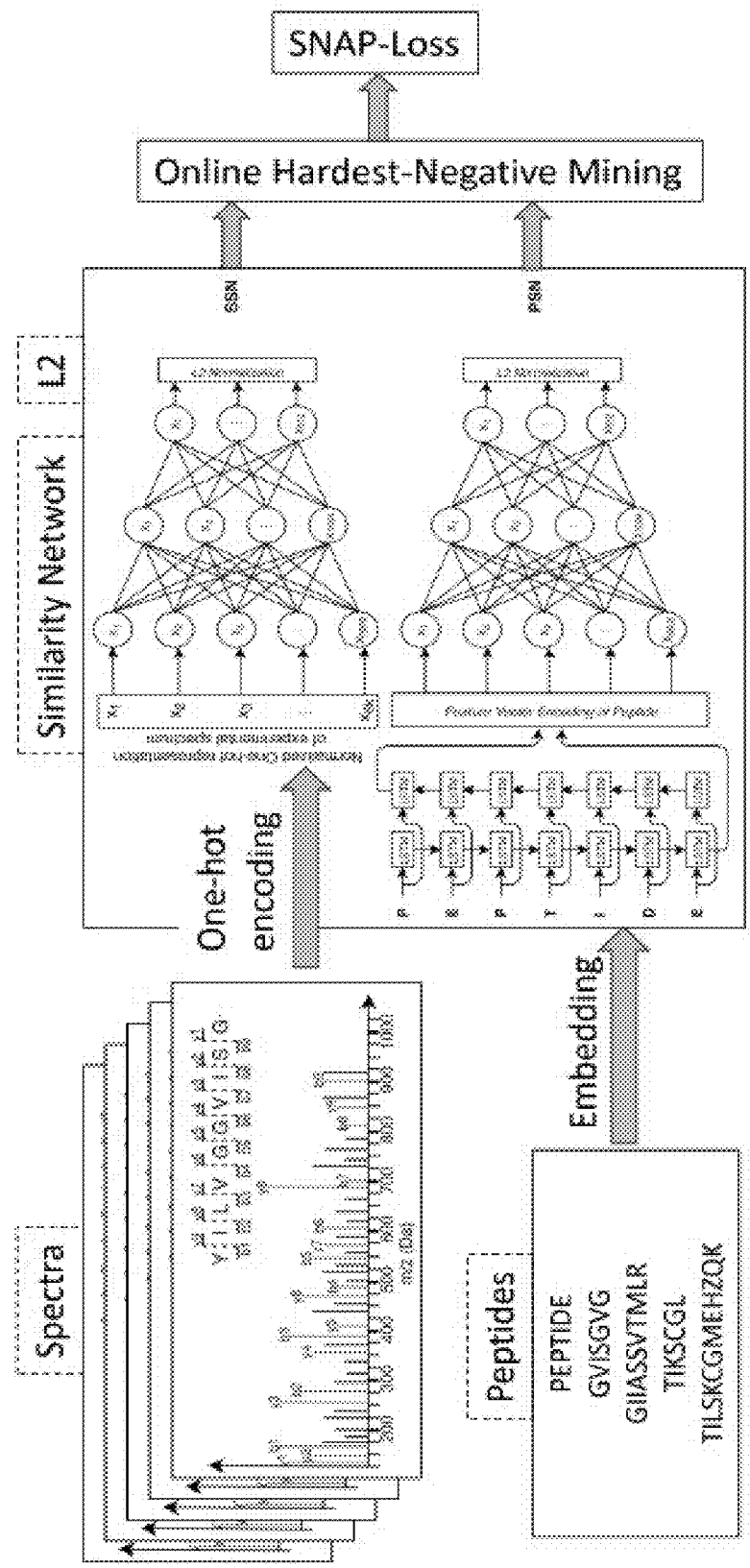
FIG. 4 shows a schematic view of a deep similarity network for proteomics, according to an embodiment of the subject invention, which can be referred to as SpeCollate. The spectra Q can be passed to a spectrum sub-network (SSN) in the form of sparse one-hot normalized representation. The positive (P) and negative (N) peptides can be passed to a peptide sub-network (PSN) one by one in a forward direction and/or a backward direction.

FIG. 4 shows a schematic view of a deep similarity network for proteomics (SpeCollate), according to an embodiment of the subject invention. Referring to FIG. 4, the spectra Q can be passed to the SSN in the form of sparse one-hot normalized representation. The positive (P) and negative (N) peptides can be passed to the PSN one by one in a forward direction and/or a backward direction.

The SSN branch of the network processes spectra and embeds them on to the surface of a unit hypersphere in a Euclidean subspace ($IR^{256}$). The SSN can include (or consist of) two fully connected hidden layers and an L2 normalization output layer. The first fully connected layer can have a size of, for example, 80,000×1024, and the second fully connected layer can have a size of, for example, 1024×256. The input layer can be of size 80,000, which takes spectra as input in the form of sparse vectors with intensity values normalized to zero mean and unit variance and mass binning of 0.1 Da. Both hidden layers can use ReLU as the activation function. A dropout mechanism (e.g., with a probability value of 0.3) can be used after the first hidden layer to avoid over-fitting.

The PSN branch of the network can process the peptides and embed them onto the surface of the same hypersphere in the Euclidean subspace ($IR^{256}$), enabling the direct comparison between spectra and peptides. The PSN can include (or consist of) one bi-directional long short-term memory (Bi-LSTM) layer followed by two fully connected layers. An embedding layer can be added before the Bi-LSTM layer to embed each amino acid character into a floating point vector (e.g., of size 256). Because there are 20 amino acids, the vocabulary size used can be 20 to construct the embeddings. Bi-LSTM can have a hidden dimension of 512, and the output from both forward pass and backward pass can be concatenated (e.g., to get an output of total length of 1024). This output can be further fed to the two fully connected layers, which can have sizes of, for example, 1024×512 and 512×256, respectively. ReLU can be used as the activation function for the fully connected layers, and a dropout (e.g., with a probability of 0.3) can be used after the Bi-LSTM and the first fully connected layer.

A training dataset can be generated from spectral libraries obtained from online repositories (e.g., NIST and MassIVE). The spectral libraries can be preprocessed to generate two sets of data (i.e., spectra and their corresponding peptides). For the examples discussed herein, about 4.8 million spectra with known peptide sources were obtained, containing about 0.5 million spectra from modified peptides. The modifications used for training the datasets included phosphorylation, oxidation, and N-terminal acetylation. Complete details of the training dataset are given in Table 1.

Spectra can be preprocessed into sparse vectors containing intensity values that are normalized to zero mean and unit variance. The charge values can be appended to the sparse vectors in one-hot encoded form. Peptides strings can be padded with the zero character to the length of 64 before feeding to the PSN. Next, the dataset can be split into disjoint training and testing subsets of size 80% and 20%, respectively. The training set can be further split into batches of 1024 samples each. The training for the examples was performed using the pytorch framework 1.6 running on python 3.7.4. For fast training, the training process was performed on NVIDIA TITAN Xp GPUs with 12 GB of memory.

TABLE 1

Details of training dataset

| Parameters | Values |
| --- | --- |
| Training Samples | 4.8M |
| Charge 2 | 2.6M |
| Charge 3 | 1.6M |
| Charge 4 | 0.4M |
| Other Charges | 1.2M |
| Unmodified Samples | 4.3M |
| Modified Samples | 0.5M |
| Max Charge | 8 |
| Number of Species | 7 |

The training process can begin with a forward pass of a batch (e.g., a subset of 1024 data points) containing experimental spectra and their corresponding (positive) peptides through the SSN and PSN, respectively. At this point, the dataset doesn't include sextuplets as the negative examples haven't been selected yet. Once a batch is forward passed through the network the four negative examples for each positive pair ($q_i \in Q$, $p_i \in P$) are mined, where Q is the set of embedded spectra and P is the set of embedded peptides. A negative tuple ($q_j$, $P_k$) for $q_i$ is mined such that $q_j$ is the closest negative spectrum to $q_i$ and $p_k$ is the closest negative peptide to $q_i$. Similarly, a negative tuple ($q_l$, $p_m$) for $p_i$ is mined such that $q_l$ is the closest negative spectrum to $p_i$ and $P_m$ is the closest negative peptide to $p_i$. Hence, a sextuplet $S=((q_i, p_i), q_{ji}, p_{ki}, q_{li}, p)$ containing a query (or anchor) spectrum, positive peptide, two negative spectra, and two negative peptides is constructed via online sextuplet mining for each positive example in the training dataset. The learning parameters are given in Table 2.

The mathematical formulation of online negative mining to generate sextuplets will now be discussed. Given a batch B containing b training samples, i.e. two sets $Q_{bar}$ and $P_{bar}$, after forwarding $Q_{bar}$ through the SSN and $P_{bar}$ through the PSN, embedded spectra $Q=f_{SSN}(Q_{bar})$ and peptides $P=f_{PSN}(P_{bar})$ are obtained, where $Q, P \subset IR^{256}$. In order to efficiently compute negative examples for each positive pair ($q_i \in Q$, $p_i \in P$), three distance matrices, $D_{Q \times Q}$, $D_{Q \times P}$, and $D_{P \times P}$, containing pairwise squared L2 distances (SED) of spectra and peptides are calculated. $D_{Q \times Q}$ contains the SED values between all spectra $\|q_i - q_j\|^2$, $D_{Q \times P}$ contains the SED values between spectra and peptides $\|q_i - p_j\|^2$, and $D_{P \times P}$ contains SED values between all peptides $\|p_i - p_j\|^2$, where $i,j \in \{1, 2, \ldots b\}$. Note that these are symmetric matrices of size b×b with diagonal containing the positive pair SEDs for $D_{Q \times P}$ and zero for $D_{Q \times Q}$ and $D_{P \times P}$. For $D_{Q \times Q}$ and $D_{P \times P}$, the distance matrix can be calculated as follows (only the calculation for $D_{Q \times Q}$ is shown, as $D_{P \times P}$ is derived in exactly the same way).

Consider the Gramian matrix of Q to be $G_Q$:

$$G_Q = \text{Gramian}(Q) = [<q_i, q_j>]$$

and the diagonal of $G_Q$ as:

$$g_Q = \text{diag}(G_Q)$$

Then, $D_{Q \times Q}$ is given by:

$$D_{Q \times Q} = g_Q 1^T - 2G_Q + 1 g_Q^T$$

where 1 is a vector containing all ones and is the same length as $g_Q$ (i.e., b). $D_{Q \times P}$ can be derived in a similar fashion as follows:

Let $$G_P = \text{Gramian}(P) = [<p_i, p_j>]$$

and $$g_P = \text{diag}(G_P)$$

Then $$D_{Q \times P} = g_Q 1^T - 2Q^T P + 1 g_P^T$$

TABLE 2

Training parameters for SpeCollate

| Parameters | Values |
| --- | --- |
| Train/Test | 0.8 |
| Learning Rate | 0.0001 |
| Optimizer | Adam |
| Weight Decay | 0.0001 |
| Num. Layers | 1 LSTM, 2 FC |
| Margin | 0.2 |

Once these matrices are calculated, the four negatives can be calculated using min function over matrices. Let the elements of matrices $D_{Q \times Q}$, $D_{Q \times P}$, and $D_{P \times P}$ be represented by $qq_{ir}$, $pp_{ir}$, and $qp_{ir}$, respectively, where i, r represent the row and the column indexes, respectively. Then, the subscripts $j_i$, $k_i$, $l_i$ and $m_i$ for the negative examples in the sextuplet S can be determined using the following four equations:

$$j_i = \underset{r, r \neq i}{\arg\min} qq_{ir}, i = 1, \ldots, b$$

$$k_i = \underset{r, r \neq i}{\arg\min} qp_{ri}, i = 1, \ldots, b$$

$$l_i = \underset{r, r \neq i}{\arg\min} qp_{ir}, i = 1, \ldots, b$$

$$m_i = \underset{r, r \neq i}{\arg\min} pp_{ir}, i = 1, \ldots, b$$

As these subscripts indicate the corresponding indices of the negative spectra and peptides in sets Q and P, they can be directly accessed for loss calculation. Once all the sextuplets are constructed in a given batch, the loss value is computed using the custom-designed SNAP-loss function. The gradient update is back-propagated through both the SSN and the PSN. The online sextuplet mining is visualized in FIG. 5.

The training objective is to minimize the SED between a given spectrum and its corresponding positive peptide while maximizing for the negative examples. In order to achieve this, an approach can be adopted similar to triplet-loss function, which works on triplets (A, P, N) with A as the anchor, P as the positive example, and N as the negative example (see also Schultz et al., Learning a distance metric from relative comparisons, In: Advances in neural information processing systems, 2004, p. 41-48; which is hereby incorporated by reference herein in its entirety). In this case, the differences between SEDs among A and P $\|A-P\|^2$, and A and N $\|A-N\|^2$ is minimized with a constant margin value added to the positive distance as shown below.

$$L = \sum_{i=0}^{b} \max(\|A - P\|^2 - \|A - N\|^2 + \text{margin}, 0)$$

This works well where data with single modality is dealt with (e.g., image verification). In many embodiments, the novel loss function (SNAP-loss) can extend triplet-loss to multi-modal data, such as numerical spectra and sequence peptides. All possible negatives ($q_j$, $p_k$, $q_l$, $p_m$) can be considered for a given positive pair ($q_i$, $p_i$) and the total loss can be averaged. The four possible negatives are explained below.

$q_j$: The negative spectrum for $q_i$.
$p_k$: The negative peptide for $q_i$.
$q_l$: The negative spectrum for $p_i$.
$p_m$: The negative peptide for $p_i$.

In order to calculate the loss value, a few variables can first be defined that are precomputed in distance matrices above as follows:

$$d_i = \|q_i - p_i\|^2$$

$$d_{n1} = \|q_i - q_j\|^2$$

$$d_{n2} = \|q_i - p_k\|^2$$

$$d_{n3} = \|p_i - q_l\|^2$$

$$d_{n4} = \|p_i - p_m\|^2$$

Then the SNAP-loss is calculated as follows:

$$L = \frac{1}{4b} \sum_{i=1}^{b} \sum_{r=1}^{4} \max(d_i - d_{nr} + \text{margin}, 0)$$

Figure 5:
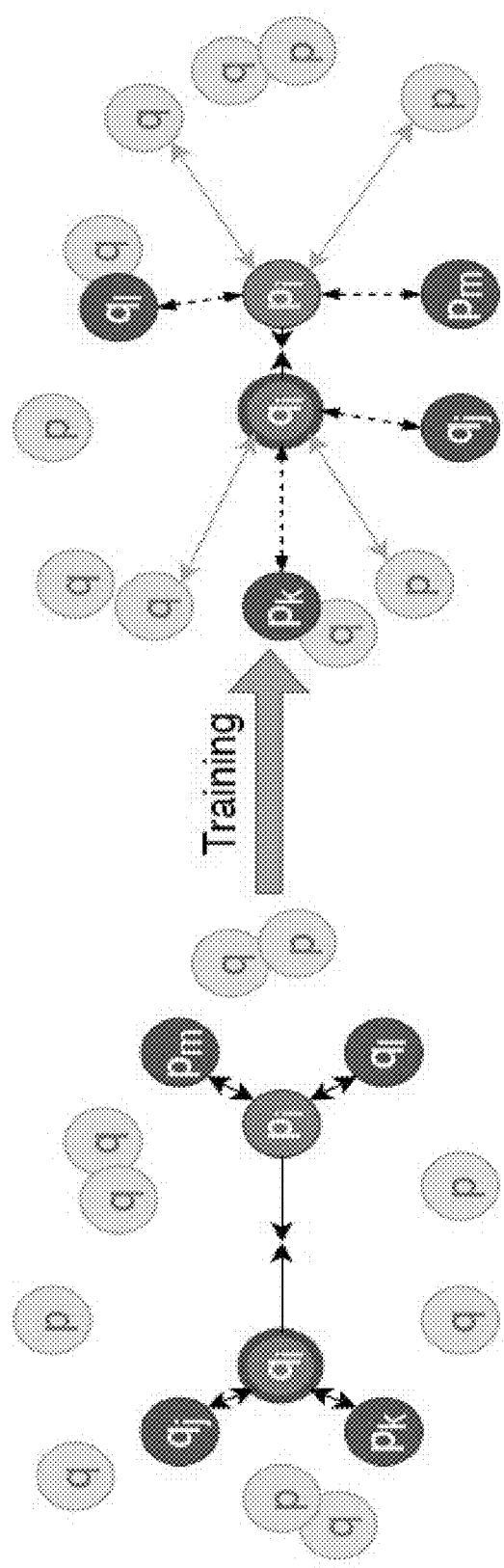
FIG. 5 shows a schematic view of online sextuplet mining for a loss function, which can be referred to as SNAP-loss. At each batch iteration, four negatives can be selected that are closest to either q or p. The gradient update can move the negatives far away, and a new set of negatives can be selected during the next iteration, and so on. This process can make sure the network learns on the hardest examples for optimum training.

The training process is visualized in FIG. 5. Once the training is complete, the similarity inference can be performed on a test dataset by simply transforming the peptides and spectra into the embedded subspace and applying the nearest neighbor search. FIG. 3 shows the resultant Euclidean space is $\mathbb{R}^{256}$, where all the peptides and spectra are projected onto.

Because a large number of spectra might need to be searched against peptides, the peptides can be indexed by precomputing the embedded feature vectors and stored for later use. Similar pre-computation can be performed for the experimental spectra before performing the search to avoid repeated encoding as each experimental spectrum needs to be searched against multiple peptides.

The L2 distance measure can be efficiently calculated (e.g., on a GPU) by computing the masked distance matrix for the peptides that fall within the precursor m/z range. Further, this process can easily scale to multiple GPUs making it feasible for large datasets. The inverse of the L2 distance can be reported as the match score.

The embodiments of the subject invention can improve the machine on which it is running by minimizing computing resource costs. This technical solution solves the technical problem of vast amounts of computing resources being required to match mass spectra and peptides on computing machines.

In order to measure the L2 distance between the embedded set of spectra Q and peptides P, Q can be split into batches (e.g., batches of size 1024). Peptides can be selected for each batch of spectra based on the precursor tolerance and their number can vary. The maximum number of peptides in a batch can be limited (e.g., to 16384) due to the memory limit (e.g., 12 GB) of the machine (e.g., a GPU). If more than the limit (e.g., 16384) fall within the precursor window, they can be further split into sub-batches and a search process can be repeated for each sub-batch. This gives two matrices $A_{1024 \times 256}$ and $B_{<16384 \times 256}$ containing a batch of spectra and a sub-batch of peptides, respectively. Parallel distance matrix $D_{A \times B}$ calculation can be performed using the following equation:

$$D_{A \times B} = g_A 1^T - 2A^T B + 1 g_B^T$$

where $g_A$ is the diagonal vector of the Gramian matrix $G_A$ of A and $g_B$ is the diagonal vector of the Gramian matrix $G_B$ of B. $D_{A \times B}$ is a 1024×≤16384 distance matrix and contains the distances of each spectrum in A to each peptide in B. Next, the mask matrix M of the same size as $D_{A \times B}$ can be computed, which contains 1 for peptides that fall within the precursor window of each spectrum and 0 for the rest. The Hadamard product of $D_{A \times B}$ and M gives the distance measure of only relevant peptide-spectrum pairs. For each spectrum, the top scoring peptide (minimum distance) is kept and the rest are discarded giving a resultant score matrix of size 1024×5, which is stored for posterior analysis later.

Embodiments of the subject invention utilize a deep similarity network for proteomics (SpeCollate) to learn a cross-modal similarity function between peptide and spectra for the purpose of identifying peptide-spectrum matches. Proteomics has entered the realm of Big-Data, and the number of labeled and annotated spectra is increasing rapidly. Related art computational techniques for peptide database search are not able to keep up with the ever growing data demand and are limited to performing database search for only moderate sized datasets. Moreover, related art methods suffer from heuristic scoring techniques and inferior quality of simulated theoretical spectra. SpeCollate marks the beginning of trend shift towards data-oriented algorithm design for peptide database search, which eliminates the inherent problems associated with numerical strategies. This is achieved by learning a cross-modal similarity function that embeds spectra and peptides in a shared Euclidean subspace for direct comparison. As the similarity function is learned, it is able to overcome the limited performance of heuristic based scoring and inaccurate spectral simulation. SpeCollate learns this similarity function by optimizing a novel loss function (SNAP-loss), which trains on sextuplets of data points to project positive examples closer to each other while pushing negative examples far from each other. By training on 4.8 million sextuplets, SpeCollate was able to achieve a remarkable test accuracy of 99% while the database search accuracy for the test dataset was as high as 99.5%.

Embodiments of the subject invention mark a paradigm shift from related art peptide-spectrum-comparing algorithms to deep learning-based cross-modal similarity networks. This provides superior performance to related art algorithms, and it can be used for peptide deductions in a peptide database search.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

When ranges are used herein, such as for dose ranges, combinations and subcombinations of ranges (e.g., subranges within the disclosed range), specific embodiments therein are intended to be explicitly included.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to embodiments of the invention.

Example 1

The network was trained (as discussed extensively above) for 200 epochs on a dataset of size ~4.8 million sextuplets. The training was performed on an NVIDIA TITAN Xp GPU installed in a server of 48-cores and 120 GBs of memory. Pytorch 1.6 was used to design the network using Python 3.7.1 on Linux 16.04. The database search was also performed on the test dataset to measure the quality of results just by comparing the embeddings.

Figure 6A:
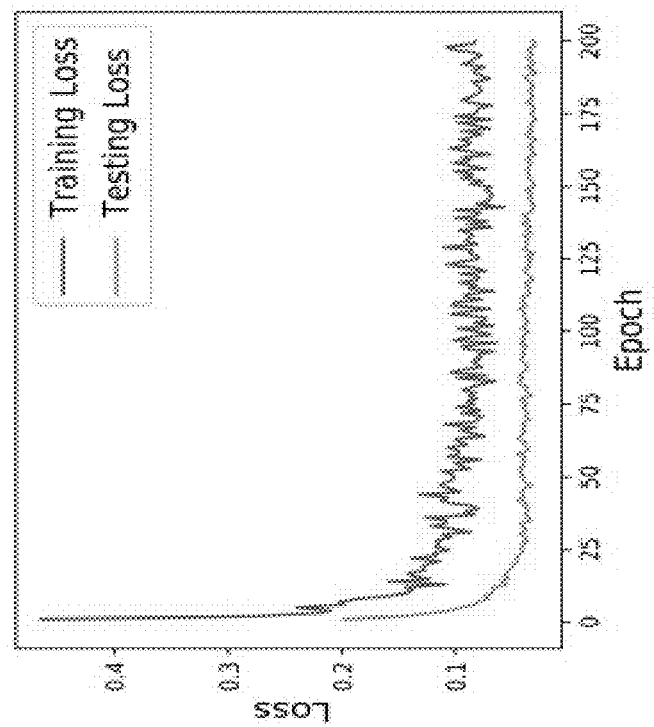
FIG. 6A shows a plot of accuracy (in percentage (%)) versus epoch, showing train/test accuracy. The (orange) curve with the higher values at each epoch is for the testing accuracy; and the (blue) curve with the lower values at each epoch is for training accuracy.
Figure 6B:
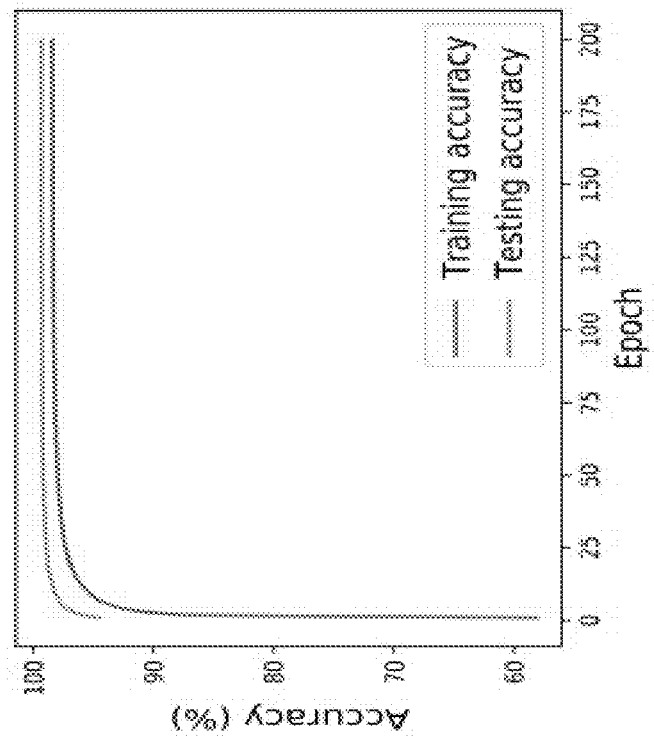
FIG. 6B shows a plot of loss versus epoch, showing train/test loss. The (orange) curve with the lower values at each epoch is for the testing loss; and the (blue) curve with the higher values at each epoch is for training loss.

The network was trained for 200 epochs to achieve validation accuracy of 99%. The accuracy was measured by the ratio of number of times the correct peptide is the closest one to the anchor spectrum to the total number of spectra in a batch. The true peptide $t_p$ is defined as a Boolean function that outputs one of the closest peptides p to the anchor q in the current batch B is the true peptide $p_q$ and zero otherwise.

$$tp(q, B) = \begin{cases} 1 & \mathrm{argmin}_{p \in B} \|q - p\|^2 = p_q \\ 0 & \text{otherwise} \end{cases}$$

$$\mathrm{Accuracy} = \frac{\sum_{q \in B} tp(q, B)}{|B|}$$

where $p_q$ is the true peptide for q, B is the current batch, and $P_B$ and $Q_B$ represent the peptides and spectra, respectively, in B. FIGS. 6A and 6B show the accuracy and loss values, respectively, for the training process.

Figure 7:
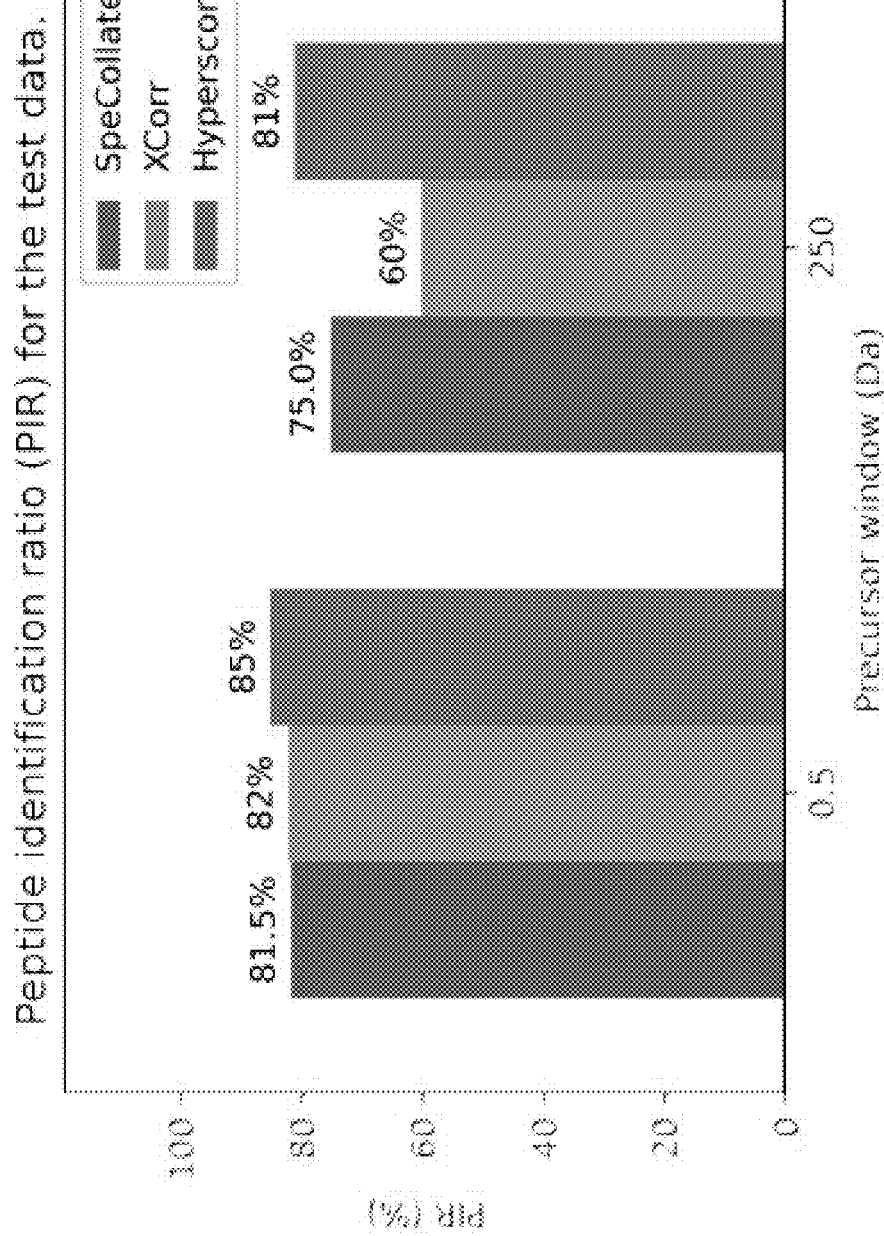
FIG. 7 shows a plot of precursor identification rate (PIR) (in %) versus precursor window (in Daltons (Da)), showing the PIR for a test dataset. PIR was measured for SpeCollate, XCorr, and Hyperscore using +/−0.5 Da and +/−250 Da precursor mass tolerance windows. SpeCollate performed comparable to XCorr and Hyperscore for the +/−0.5 Da window while SpeCollate significantly outperformed XCorr and stayed on par with Hyperscore for the +/−250 Da window. The left-most (blue) bar at both 0.5 Da and 250 Da is for an embodiment of the subject invention (labeled as "SpeCollate" in FIG. 7); the middle (orange) bar at both 0.5 Da and 250 Da is for XCorr; and the right-most (green) bar at both 0.5 Da and 250 Da is for Hyperscore.
Figure 8B:
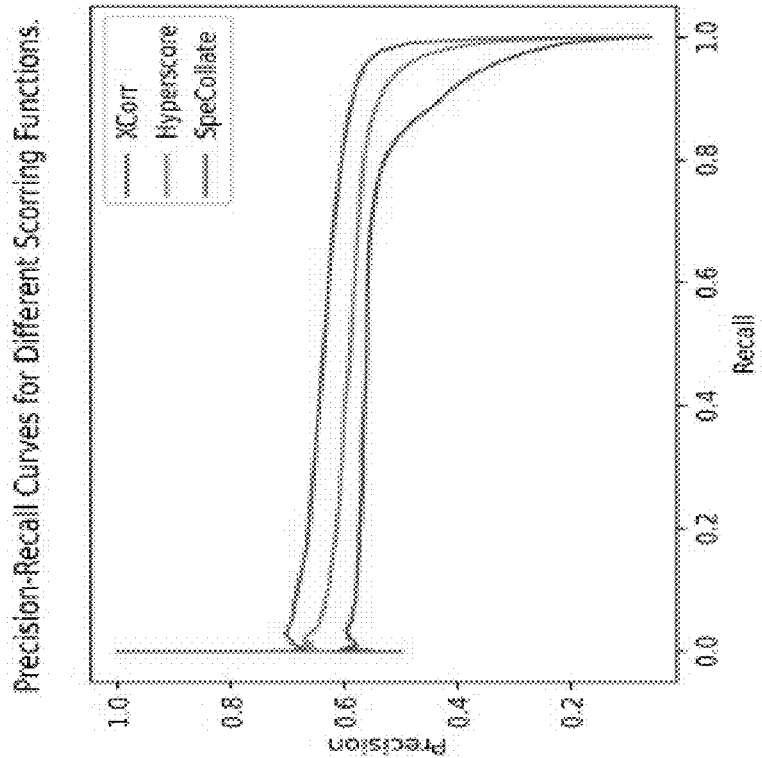
FIG. 8B shows a plot of precision versus recall for a closed search using SpeCollate, XCorr, and Hyperscore. The (green) curve with the highest precision value at recall=0.2 is for an embodiment of the subject invention (labeled as "SpeCollate" in FIG. 8B); the (orange) curve with the second-highest precision value at recall=0.2 is for Hyperscore; and the (blue) curve with the lowest precision value at recall=0.2 is for XCorr. SpeCollate performed the best of the three (+/−0.5 Da precursor mass tolerance).
Figure 8A:
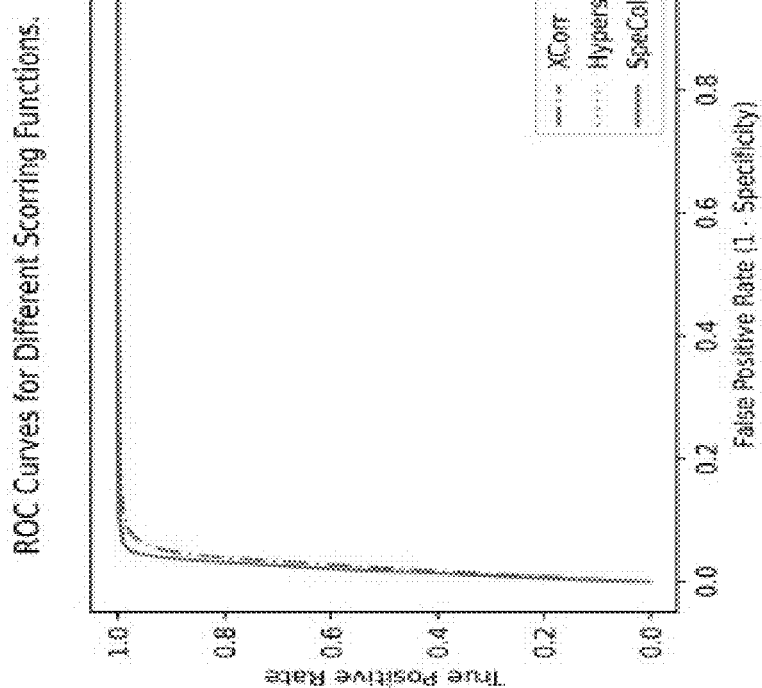
FIG. 8A shows a plot of true positive rate versus false positive rate (1—specificity), showing the receiver operating characteristic (ROC) curve for a closed search using SpeCollate, XCorr, and Hyperscore. The solid (green) curve is for an embodiment of the subject invention (labeled as "SpeCollate" in FIG. 8A); the dotted (orange) curve is for Hyperscore; and the dashed/dotted (blue) curve is for XCorr. SpeCollate performed the best of the three (+/−0.5 Da precursor mass tolerance).
Figure 9B:
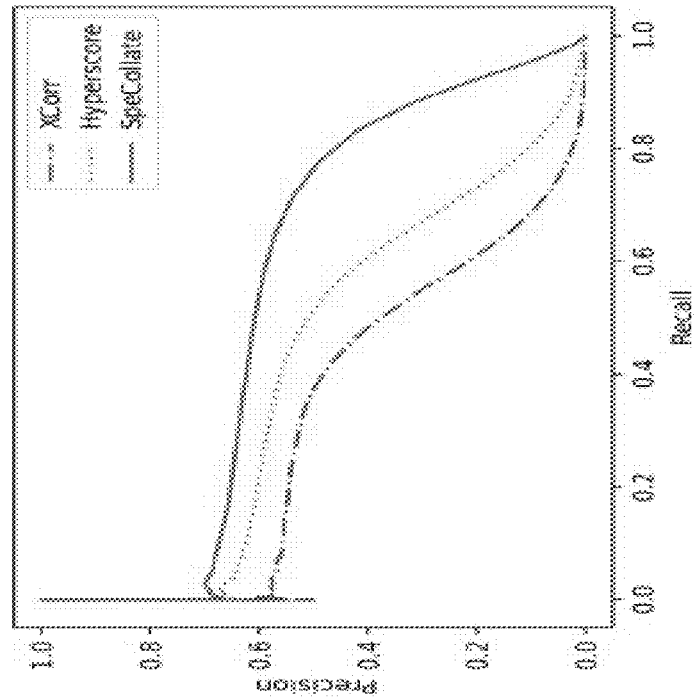
FIG. 9B shows a plot of precision versus recall for a closed search using SpeCollate, XCorr, and Hyperscore. The solid (green) curve with the highest precision value at recall=0.2 is for an embodiment of the subject invention (labeled as "SpeCollate" in FIG. 9B); the dotted (orange) curve with the second-highest precision value at recall=0.2 is for Hyperscore; and the dashed/dotted (blue) curve with the lowest precision value at recall=0.2 is for XCorr. SpeCollate performed the best of the three (+/−250 Da precursor mass tolerance).
Figure 9A:
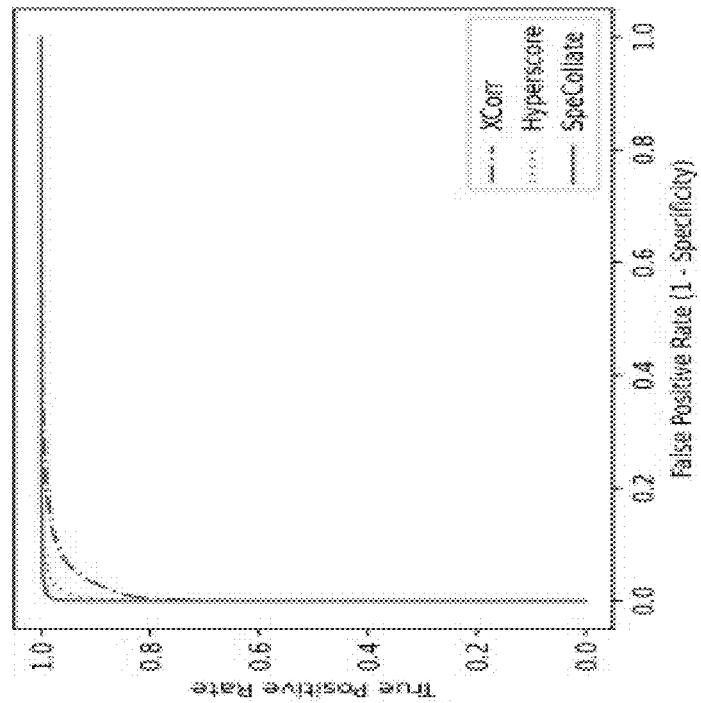
FIG. 9A shows a plot of true positive rate versus false positive rate (1—specificity), showing the receiver operating characteristic (ROC) curve for an open search using SpeCollate, XCorr, and Hyperscore. The solid (green) curve is for an embodiment of the subject invention (labeled as "SpeCollate" in FIG. 9A); the dotted (orange) curve is for Hyperscore; and the dashed/dotted (blue) curve is for XCorr. SpeCollate performed the best of the three (+/−250 Da precursor mass tolerance).

The similarity inference was then performed for a test dataset containing 46,000 spectra corresponding to 35,000 peptides, and the peptide identification ratio (PIR) was compared against the related art XCorr and Hyperscore scoring functions. The dataset for the evaluation was a subset of the NIST Human Phosphopeptide Label Free Library and was not used for training of validation purposes. This dataset was kept for testing purposes due to the limited number of modifications (per peptide) as the model is only able to match peptides with one modification. Only samples with either no modification or a single modification were selected. Modifications are limited to phosphorylation and oxidation and spectra with charge value 5+ or less were used. PIR is defined as follows:

$$PIR = \frac{\sum_{q \in Q} tp(q, B_F)}{|B|}$$

where $B_F$ represents the peptides that fall within the precursor mass filter and Q represents the spectra set. FIG. 7 shows the PIR values for the three scoring functions. As can be seen, SpeCollate performed on par with the two state-of-the-art scoring functions for a +/−0.5 Da precursor mass tolerance window. On the other hand, for a +/−250 Da mass window, SpeCollate significantly outperformed XCorr while giving comparable results to Hyperscore.

The receiver operating characteristic (ROC) curves were also plotted, as were precision-recall curves, for comparing the performance of the three scoring functions. Referring to FIGS. 8A, 8B, 9A, and 9B, SpeCollate performed significantly better than XCorr and Hyperscore in both open (FIGS. 9A and 9B) and closed (FIGS. 8A and 8B) search. It is noted that ROC curves tend to overestimate the skill of a model, especially for open search, when the classes are not balanced and there are far more true-negatives than false-positives (with a rate that stays close to zero). Therefore, for a scenario where positive examples are far more valuable than the negative ones (such is the case when searching for a peptide-spectrum match), precision-recall curves (FIGS. 8B and 9B) better represent the performance as the true-negatives are not considered for either precision or recall calculation.

As seen in the results, the systems and methods of embodiments of the subject invention (using SpeCollate) mark a paradigm shift and move towards MS based proteomics database search using deep learning. By eliminating the need for approximate scoring functions and unsophisticated spectrum simulators, SpeCollate significantly simplifies the database search process and shows that deep learning methods can achieve performance on par with the state-the-of-art related art systems and methods. Moreover, SpeCollate reduces the search space by orders of magnitude by allowing the spectrum of any charge to be compared directly against the peptide. Similarly, the network (SpeCollate) can be trained to match the modified spectra to their original unmodified peptides, further reducing the search space and leading to improved search times and false-discovery rates.

The observed recall values, shown in FIG. 7, are as expected because the recall values of the related art scoring functions pose an upper bound for the trained network performance as the labeled datasets are generated using the same functions. SpeCollate demonstrates its efficiency by performing marginally close to these functions.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A system for measuring cross-modal similarity between mass spectra and peptides, the system comprising:
    a processor; and
    a machine-readable medium in operable communication with the processor and having instructions stored thereon that, when executed by the processor, perform the following steps:
        receiving a set of mass spectra data and a set of peptide data into a network comprising a spectral sub-network (SSN) and a peptide sub-network (PSN);
        inputting the set of mass spectra data into the SSN, the SSN comprising two fully connected hidden layers and an L2 normalization output layer;
        inputting the set of peptide data into the PSN, the PSN comprising one bi-directional long short-term memory (Bi-LSTM) layer and two fully connected layers;
        processing the set of mass spectra data in the SSN and embedding it on a surface of a unit hypersphere in a Euclidean subspace;
        processing the set of peptide data in the PSN and embedding it on the surface of the unit hypersphere in the Euclidean subspace; and
        matching mass spectra from the set of mass spectra data with peptides from the set of peptide data, using an L2-distance-based similarity measure.

2. The system according to claim 1, the instructions when executed further performing the following step:

training the network on a loss function that calculates
gradients from sextuplets of data points of the set of
mass spectra data, the set of peptide data, or both.

3. The system according to claim 2, the training of the network comprising calculating a loss value by generating the sextuplets after each forward pass,
each sextuplet comprising a positive pair (Q, P), a negative pair $(Q_N, P_N)_Q$ for Q, and a negative pair $(Q_N, P_N)_P$ for P, where Q is an anchor spectrum and P is a positive peptide.

4. The system according to claim 3, each negative pair being selected via an online hardest negative mining process, in which negative spectra and peptides that are closest to Q and P are selected for a given batch after each forward pass.

5. The system according to claim 1, the PSN further comprising an embedding layer before the Bi-LSTM layer.

6. The system according to claim 5, the embedding layer using a vocabulary size of 30 to construct embeddings.

7. The system according to claim 1, the Bi-LSTM layer having a hidden dimension of 512, and
the two fully connected layers of the PSN comprising a first layer with a size of 1024×512 and a second layer with a size of 512×256.

8. The system according to claim 1, the two fully connected hidden layers of the SSN comprising a first layer with a size of 80,000×1024 and a second layer with a size of 1024×256.

9. The system according to claim 1, the two fully connected hidden layers of the SSN utilizing a rectified linear activation function (ReLU),
the SSN further comprising a dropout mechanism with a probability of 0.3 after a first layer of the two fully connected hidden layers of the SSN and before a second layer of the two fully connected hidden layers of the SSN.

10. The system according to claim 1, the two fully connected layers of the PSN utilizing a rectified linear activation function (ReLU),
the PSN further comprising:
a first dropout mechanism with a first probability of 0.3 after the Bi-LSTM layer and before a first layer of the two fully connected layers of the PSN; and
a second dropout mechanism with a second probability of 0.3 after the first layer of the two fully connected layers of the PSN and before a second layer of the two fully connected layers of the PSN.

11. A method for measuring cross-modal similarity between mass spectra and peptides, the method comprising:
receiving, by a processor, a set of mass spectra data and a set of peptide data into a network comprising a spectral sub-network (SSN) and a peptide sub-network (PSN);
inputting, by the processor, the set of mass spectra data into the SSN, the SSN comprising two fully connected hidden layers and an L2 normalization output layer;
inputting, by the processor, the set of peptide data into the PSN, the PSN comprising one bi-directional long short-term memory (Bi-LSTM) layer and two fully connected layers;
processing, by the processor, the set of mass spectra data in the SSN and embedding it on a surface of a unit hypersphere in a Euclidean subspace;
processing, by the processor, the set of peptide data in the PSN and embedding it on the surface of the unit hypersphere in the Euclidean subspace; and
matching, by the processor, mass spectra from the set of mass spectra data with peptides from the set of peptide data, using an L2-distance-based similarity measure.

12. The method according to claim 11, further comprising:
training, by the processor, the network on a loss function that calculates gradients from sextuplets of data points of the set of mass spectra data, the set of peptide data, or both.

13. The method according to claim 12, the training of the network comprising calculating a loss value by generating the sextuplets after each forward pass,
each sextuplet comprising a positive pair (Q, P), a negative pair $(Q_N, P_N)_Q$ for Q, and a negative pair $(Q_N, P_N)_P$ for P, where Q is an anchor spectrum and P is a positive peptide.

14. The method according to claim 13, each negative pair being selected via an online hardest negative mining process, in which negative spectra and peptides that are closest to Q and P are selected for a given batch after each forward pass.

15. The method according to claim 11, the PSN further comprising an embedding layer before the Bi-LSTM layer, the embedding layer using a vocabulary size of 30 to construct embeddings.

16. The method according to claim 11, the Bi-LSTM layer having a hidden dimension of 512, and
the two fully connected layers of the PSN comprising a first layer with a size of 1024×512 and a second layer with a size of 512×256.

17. The method according to claim 11, the two fully connected hidden layers of the SSN comprising a first layer with a size of 80,000×1024 and a second layer with a size of 1024×256.

18. The method according to claim 11, the two fully connected hidden layers of the SSN utilizing a rectified linear activation function (ReLU),
the SSN further comprising a dropout mechanism with a probability of 0.3 after a first layer of the two fully connected hidden layers of the SSN and before a second layer of the two fully connected hidden layers of the SSN.

19. The method according to claim 11, the two fully connected layers of the PSN utilizing a rectified linear activation function (ReLU),
the PSN further comprising:
a first dropout mechanism with a first probability of 0.3 after the Bi-LSTM layer and before a first layer of the two fully connected layers of the PSN; and
a second dropout mechanism with a second probability of 0.3 after the first layer of the two fully connected layers of the PSN and before a second layer of the two fully connected layers of the PSN.

20. A system for measuring cross-modal similarity between mass spectra and peptides, the system comprising:
a processor; and
a machine-readable medium in operable communication with the processor and having instructions stored thereon that, when executed by the processor, perform the following steps:
receiving a set of mass spectra data and a set of peptide data into a network comprising a spectral sub-network (SSN) and a peptide sub-network (PSN);
inputting the set of mass spectra data into the SSN, the SSN comprising two fully connected hidden layers and an L2 normalization output layer;

inputting the set of peptide data into the PSN, the PSN comprising one bi-directional long short-term memory (Bi-LSTM) layer and two fully connected layers;

processing the set of mass spectra data in the SSN and embedding it on a surface of a unit hypersphere in a Euclidean subspace;

processing the set of peptide data in the PSN and embedding it on the surface of the unit hypersphere in the Euclidean subspace;

training the network on a loss function that calculates gradients from sextuplets of data points of the set of mass spectra data, the set of peptide data, or both; and matching mass spectra from the set of mass spectra data with peptides from the set of peptide data, using an L2-distance-based similarity measure, the training of the network comprising calculating a loss value by generating the sextuplets after each forward pass, each sextuplet comprising a positive pair (Q, P), a negative pair $(Q_N, P_N)_Q$ for Q, and a negative pair $(Q_N, P_N)_P$ for P, where Q is an anchor spectrum and P is a positive peptide, each negative pair being selected via an online hardest negative mining process, in which negative spectra and peptides that are closest to Q and P are selected for a given batch after each forward pass, the PSN further comprising an embedding layer before the Bi-LSTM layer, the embedding layer using a vocabulary size of 30 to construct embeddings, the Bi-LSTM layer having a hidden dimension of 512, the two fully connected layers of the PSN being after the Bi-LSTM layer and comprising a first layer with a size of 1024×512 and a second layer with a size of 512×256, the two fully connected hidden layers of the SSN comprising a first layer with a size of 80,000×1024 and a second layer with a size of 1024×256, the two fully connected hidden layers of the SSN utilizing a rectified linear activation function (ReLU), the SSN further comprising an SSN dropout mechanism with a probability of 0.3 after the first layer of the SSN and before the second layer of the SSN, the two fully connected layers of the PSN utilizing an ReLU, and the PSN further comprising:
  a first PSN dropout mechanism with a first probability of 0.3 after the Bi-LSTM layer and before the first layer of the PSN; and
  a second PSN dropout mechanism with a second probability of 0.3 after the first layer of the PSN and before the second layer of the PSN.

* * * * *